United States Patent [19]

Hofmann et al.

[11] Patent Number: 4,676,974

[45] Date of Patent: Jun. 30, 1987

[54] BREATH TEST FOR PANCREATIC EXOCRINE FUNCTION

[75] Inventors: Alan F. Hofmann, La Jolla, Calif.; Stephen G. Cole, Toronto, Canada

[73] Assignee: The Regents of the University of California, Berkeley, Calif.

[21] Appl. No.: 611,513

[22] Filed: May 17, 1984

[51] Int. Cl.$^4$ .......................... A61K 49/00; C12Q 1/44; G01N 53/48; G01N 37/00

[52] U.S. Cl. .......................................... 424/9; 435/19; 436/56; 436/57; 436/900

[58] Field of Search ................. 435/19; 424/9; 436/56, 436/57, 900, 133

[56] References Cited

U.S. PATENT DOCUMENTS 3,844,894  10/1974  Kronick et al. .................. 436/57 X
3,917,812  11/1975  Woog et al. ........................ 424/9 X

OTHER PUBLICATIONS

Blomstrand et al., "Acta Chir. Scand.", 134:667-669 (1968).

*Primary Examiner*—David M. Naff
*Attorney, Agent, or Firm*—Brown, Martin, Haller & Meador

[57] ABSTRACT

Pancreatic exocrine function is determined by a breath test method wherein a radioactive labelled ester such as cholesterol octanoate is ingested in the body and is hydrolyzed by pancreatic enzymes and oxidized to labelled $CO_2$ which is expired in the breath. The rate of appearance of labelled $CO_2$ in the breadth is a function of the rate of hydrolysis by pancreatic enzymes which in turn reflects pancreatic exocrine function. Before ingestion, the ester is mixed with a carrier substrate such as a triglyceride to form a lipid matrix containing the ester and the lipid matrix is suspended in aqueous solution. To insure that low levels of expired labelled $CO_2$ is due to pancreatic exocrine insufficiency, the ester is ingested simultaneously with a differentially labelled unesterfied carboxylic acid or the test method is repeated with an added step of simultaneously ingesting the ester with exogenously provided pancreatic enzymes.

12 Claims, 3 Drawing Figures

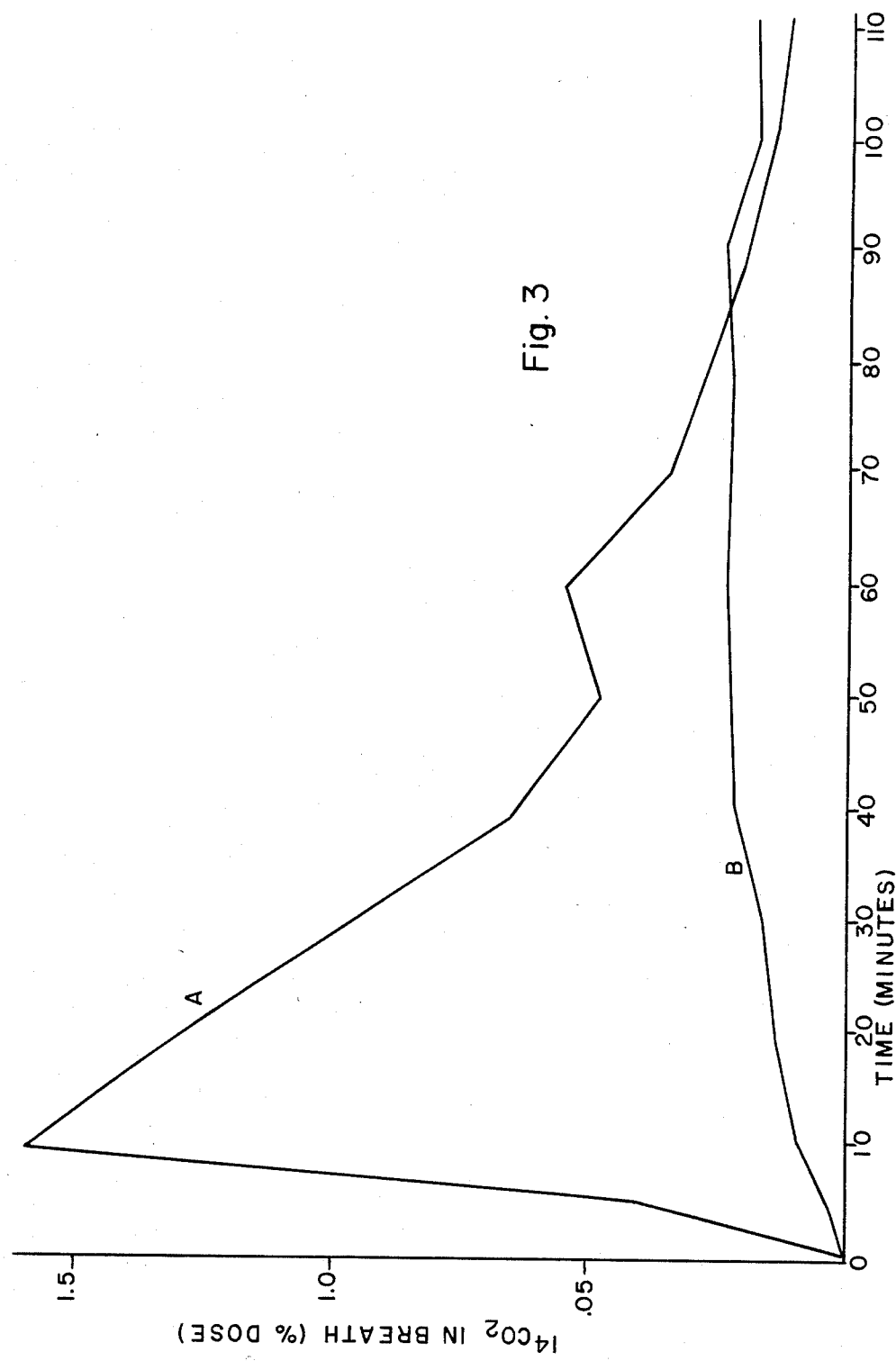

BREATH TEST FOR PANCREATIC EXOCRINE FUNCTION

ACKNOWLEDGEMENT

This invention was made with Government support under Grant No. AM 21506 awarded by the National Institute of Health, Department of Health and Human Services. The Government has certain rights in this invention.

FIELD OF INVENTION

This invention relates to a breath test method for assessing pancreatic exocrine function.

BACKGROUND OF THE INVENTION

Although there exists a variety of tests currently used to assess pancreatic exocrine function none have the combined features of reliability, ease of performance or are rapid in yielding results. The principles and problems of breath tests are discussed in a paper by Lo and co-authors in *Advances in Pediatrics,* Vol. 29, pp. 105-127 (1982).

Tests to ascertain pancreatic exocrine function are generally categorized as direct or indirect. Direct tests as described by Lankisch in *GUT,* Volume 23, pp. 777-798 (1982), involve measuring biochemical parameters, most often enzymes, secreted in duodenal juice after exogenous hormonal stimulation of the pancreas. The major technical problem associated with Direct tests is that duodenal intubation by professional personnel is required; the procedure is expensive and uncomfortable to the patient. In addition, the location of the tube must be confirmed by fluoroscopy, and when such is done, the patient receives radiation exposure. In addition, the patient has the discomfort (and possible major side effects) caused by the intravenous administration of a hormone. Finally, there is the problem of incomplete recovery of duodenal secretions, which to be properly corrected for, requires the additional use of a recovery marker.

Indirect tests are distinguishable from Direct tests in that they make use of nutrients, generally a meal fed to the patient, in lieu of exogeneously administered hormones, to stimulate pancreatic function. Indirect tests are subdivided into two classes, those that require duodenal intubation, and those that do not. The disadvantages of Indirect tests that utilize intubation methods are similar to those associated with Direct tests. That is, the act of collecting duodenal juice is technically demanding, painful, involves radiation exposure and is subject to quantitative uncertainties. Indirect tests that do not require intubation are not subject to the technical difficulties of duodenal fluid collection, or intubation. These tests generally require that a patient ingest a meal to stimulate pancreatic function with an enzymatic substrate that is acted on by pancreatic enzymes in the duodenum. The substrate is hydrolyzed and the products are absorbed from the intestine, enter the blood stream and may subsequently be excreted. They may be measured in blood, urine, stool or breath. The prior art shows the existence of several Indirect tests. One of these, as described by Kimura and coworkers in *Digestion,* Vol. 21, pp. 133-139 (1981), is based on the hydrolysis of an amino acid derivative, N-benzoyl-L-tyrosyl-p-aminobenzoic acid (NBT-PABA), by the pancreatic enzyme chymotrypsin in the duodenum. Hydrolysis by chymotrypsin causes the release of p-aminobenzoic acid which is measured in serial blood samples or in the urine after a six to nine hour collection period. A second test as described by Kaffornick and coworkers in *Munch. Med. Wochenschr,* Vol. 119, pp. 1467-1470 (1977), involves the ingestion of fluorescein dilaurate with a meal followed by measuring the amount of fluorescein released by pancreatic esterase. The fluorescein may be measured in serial blood samples. Alternatively, urine is collected for ten hours before being analyzed for fluorescein content. The reliability of both of these tests is subject to interfering chemicals in the urine, and the urinary excretion of both products (PABA and fluorescein) may not be complete.

There have been several previous unsuccessful attempts to establish breath tests to assess pancreatic function. Both are premised on measuring the amount of $^{14}CO_2$ expired in the breath that is derived from labelled fatty acid, which has been liberated by pancreatic lipase hydrolysis of either triglyceride or trioleoylglycerol esters followed by subsequent absorbtion and oxidation in the body of the radioactive fatty acid. For several reasons, however, neither test has proved useful. Utilization of triglycerides as described by Ghoos and co-workers in *Digestion,* Vol 22, pp. 239-249 (1981), as a substrate for pancreatic esterases where a radioactive fatty acid occupies the two position of the molecule prevents rapid liberation of the fatty acid since the two position of the triglyceride is not cleaved by pancreatic esterases. Accordingly, the fatty acid can only be cleaved after it isomerizes to the one position, a process that could be rate limiting in the oxidation of the radioactive fatty acid, and hence lead to incorrect conclusions concerning pancreatic exocrine function. Alternatively, the two ester might be absorbed in the body intact and subsequently hydrolyzed by enterocyte enzymes, in which case hydrolysis of the molecule would not be an accurate indication of pancreatic exocrine function. Similarly, King and coworkers have shown in *Gastroenterology,* Vol. 84, pp. 1208 (1983) that the use of trioleoylglycerol, commonly known as triolein, containing radioactive oleic acid as a substrate for pancreatic esterases is not reliable since oleic acid is absorbed more slowly by the intestinal mucosa, and, moreover is reesterified in the enterocyle and only slowly and incompletely oxidized to $^{14}CO_2$.

It is apparent that both the Direct and Indirect tests currently used to assess pancreatic exocrine function have several shortcomings. Specifically, these tests variously require intubation, multiple blood samples or lengthy collection of urine or breath samples [6-10 hours], are subject to interfering chemicals, and may not be specific indicators of pancreatic function.

SUMMARY OF THE INVENTION

According to this invention, a novel Indirect test is presented for assessing pancreatic exocrine function including the ingestion of a labelled ester of the form R2COOR1 where R2 is a carboxylic acid esterified to a primary or secondary alcoholic group on cholesterol or any similar sterol, aliphatic, aryl, or alkyl molecule (R1). R2 includes one or more $^{14}C$ or $^{13}C$ carbon atoms that upon hydrolysis of the ester by pancreatic enzymes in the duodenum, is absorbed into the blood and subsequently oxidized to labelled $CO_2$ in the liver. The latter is expired in the breath, and the rate of appearance of $^{14}CO_2$ or $^{13}CO_2$ is a function of the rate of hydrolysis by pancreatic enzymes which in turn reflects pancreatic exocrine function.

The advantages of this breath test over other Indirect tests are fourfold: first, the need for repeated blood samples or lengthy urine collections is eliminated; second, the test is completed in a maximum of four hours and no chemical analyses are necessary; third, the unpleasant procedure for intubation is not necessary; and, fourth, the measurement of $^{14}CO_2$ or $^{13}CO_2$ in the breath is not subject to interference by other chemicals.

BRIEF DESCRIPTION OF THE DRAWINGS

FIG. 3 shows the time course of $^{14}CO_2$ levels present in the breath of zein induced pancreatic insufficient rats that either did, Curve A, or did not, Curve B, ingest exogenous pancreatic enzymes.

DETAILED DESCRIPTION OF INVENTION

Figure 1:
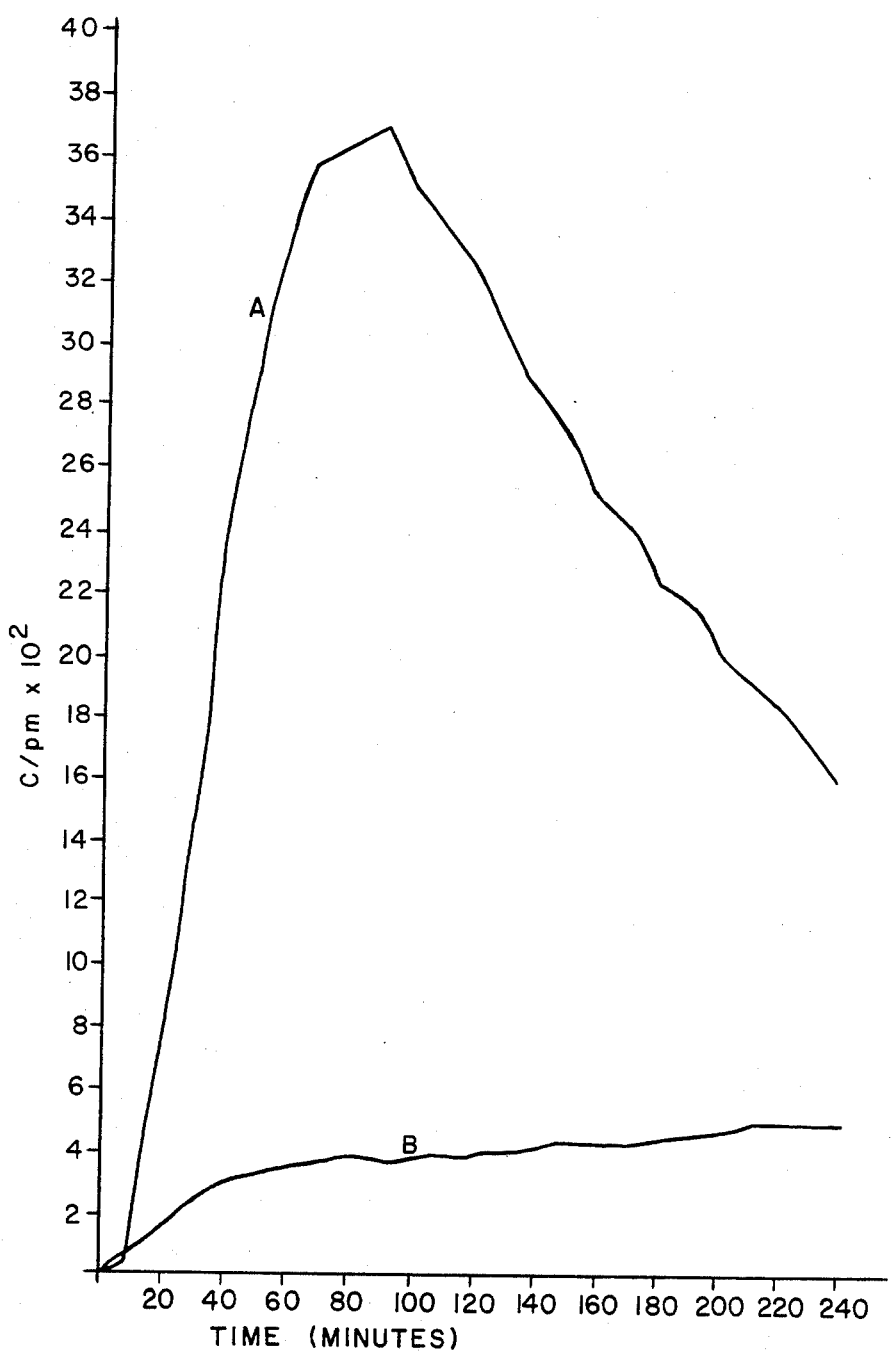
FIG. 1 shows the time course of $^{14}CO_2$ levels present in the breath of a patient with pancreatic insufficiency that either did ingest (Curve A) or did not ingest (Curve B) exogenous pancreatic enzymes.

The invention described herein is a novel breath test for assessing pancreatic exocrine function that includes the use of an ester, R2COOR1. R1 can be any sterol, aliphatic, aryl, or alkyl molecule containing an alcoholic group that is esterified to a labelled carboxylic acid, R2, that is selected for its ability to pass through the gut and be rapidly and efficiently metabolized to $CO_2$. Suitable examples include C2-C10 fatty acids, or any other group that can act as a substrate for pancreatic enzymes (and no other enzymes) such that when hydrolyzed are rapidly absorbed into the body and metabolized to $CO_2$. Examples of the latter include, but are not limited to, pyruvate and lactate. R2 is labelled with one or more $^{14}C$ or $^{13}C$ carbon atoms of sufficient specific activity (or atoms percent excess) so that when R2 is metabolized the labelled $CO_2$ expired in the breath in the form of $^{14}CO_2$ or $^{13}CO_2$ can be detected by chemical or physical methods.

To test for pancreatic exocrine function, the labelled ester substrate is mixed with a suitable amount of non-labelled carrier substrate, emulsified in water using gum acacia and a high speed blender, added to a liquid meal and ingested by a patient who has previously fasted for several hours. The non-labeled substrate can form a lipid matrix about the labeled substrate alone or with the addition of lecithin or vegetable oil.

The substrate is acted on by pancreatic esterase in the duodenum which results in the hydrolysis of the ester linkage, and liberation of the carboxylic acid that is absorbed from the intestine into the portal blood by which it travels to the liver. There it is oxidized ultimately via the tricarboxylic acid cycle, finally yielding either $^{14}CO_2$ or $^{13}CO_2$, that are expired in the breath. The amount of $CO_2$ present as $^{14}CO_2$ is determined by trapping the radioactive carbon dioxide in a solution containing a chemical trapping agent, and the amount of radioactivity determined by scintillation counting. The amount of $^{13}CO_2$ present is measured by an appropriate technique such as mass spectroscopy or infrared analysis. Abnormal pancreatic function is indicated by a low rate of hydrolysis of the labelled ester substrate which in turn is reflected by low levels of $^{14}CO_2$ or $^{13}CO_2$ in the breath.

In order to insure that low levels of expired labelled $CO_2$ is due to pancreatic exocrine insufficiency, one of two procedures is carried out. First, the ester R2COOR1, where R2 consists of $^{14}C$, is ingested simultaneously with unesterified R2 consisting of $^{13}C$. The latter can be the salt of C2-C10 fatty acids R3COOH. Thus the difference in the rate of appearance of $^{13}C$ and $^{14}C$ in the breath as carbon dioxide gives the rate of hydrolysis of the substrate R2COOR1. The amount of $^{13}CO_2$ is measured using an infrared analyzer while the amount of $^{14}CO_2$ may be measured by scintillation counting as described above. Second, several days after the initial test the procedure is repeated but with the added step that the patient simultaneously ingests radioactive R2COOR1 plus exogenously provided pancreatic enzymes. The amount of radioactive $CO_2$ expired under these conditions is again measured. If the amount of radioactive $CO_2$ expired is greater in the presence of exogeneously added pancreatic enzymes compared to the amounts previously measured in their absence, the difference is attributable to pancreatic exocrine insufficiency.

The following examples are given to aid in understanding the invention but the invention is not limited to the particular procedures, conditions or materials of the examples. It will be particularly understood by those skilled in the art that the salts of fatty acids and the corresponding fatty acids are interchangeably useable in the instant invention.

EXAMPLE 1

Two grams of crystalline, non-radioactive cholesterol octanoate was synthesized by coupling octanolyl chloride and cholesterol in the usual manner (cf Mattson, F H & Volpenhein, R A J Lipid Res., 1962, 3:281). This is dissoled in 18 ml of cholesterol-free vegetable oil at a temperature of 90° C. To this material is added 4.4 microcuries of $^{14}C$-labelled cholesterol octanoate (prepared in the same manner from cholesterol and $^{14}C$-octanoate) in heptane, and the temperature of the mixture reduced to 65° C. This mixture is termed Mixture A. Alternatively, cholesterol $^{13}C$-octanoate can be used. In this case, 1.5 gms of non-radioactive cholesterol octanoate and 0.5 gms of cholesterol octanoate-1-$^{13}C$ are used.

In a separate 500 ml beaker 10–15 ml of glycerin is added to 20 grams of gum acacia and mixed until it exhibits the consistency of a loose paste at which time the following are added: 267 ml of normal saline, 133 ml of distilled water, 5 grams of D-xylose, and 60 ml of hypotonic flavouring solution such as low sodium V8 tomato juice. This mixture is mixed with stirring on a hot plate at a temperature of 60° C. and is termed Mixture B.

Mixture A containing $^{14}C$-labelled cholesterol octanoate is added to Mixture B dropwise over a period of 5 minutes. Next, this combination of mixtures, A and B, is blended at high speed in a Waring blender for 5 minutes to yield an emulsion that is suitable for use for up to two weeks if stored at 4° C. If the emulsion is not going to be used immediately, then on the day of the study it is rehomogenized for 5 minutes, again using a Waring blender at high speed. The combination of mixtures A and B is termed Mixture C.

Prior to ingestion of Mixture C by a patient with documented pancreatic insufficiency, the emulsion was warmed to 37° C. and then all of it was drunk over a period of 2 to 5 minutes. Prior to drinking Mixture C the patient fasts for 8 hours. If the test involves measuring $^{14}CO_2$, breath samples are taken at 10 minute-intervals by having the patient exhale through a plastic tube, the outlet of which is submerged in 4 ml of a carbon dioxide trapping solution made up in a vial suitable for use in scintillation counting that includes hyamine hydroxide and absolute ethanol in a ratio of 1:1 plus 0.24 mg of thymolphthalein. This trapping solution is blue initially but turns colorless when 2 millimoles of carbon dioxide have been trapped which neutralizes the hyamine hydroxide. Breath samples are collected over a period of 4 hours which 10 ml of a non-acidic laboratory scintillation counting solution is added to each vial, and the vials stored in darkness (to eliminate chemiluminescence) for 48 hours before the amount of radioactive carbon dioxide is determined by liquid scintillation counting.

FIG. 1 shows the results obtained from a patient with documented pancreatic exocrine insufficiency. Note that these data were collected on two separate days. On Day 1 the patient ingested solution C alone, while on Day 2 he ingested solution C plus exogenously added pancreatic enzymes in the form of a tablet including $6.5 \times 10^3$, $3.2 \times 10^4$, and $4.8 \times 10^4$ USP units of lipase, protease and amylase respectively. Curve B (FIG. 1) generated on Day 1 shows low amounts of radioactive $CO_2$ in the breath over four hours. Curve A (FIG. 1) generated on Day 2 shows a dramatic increase in the amount of radioactive $CO_2$ in the breath with time. The latter is caused by the exogeneously supplied pancreatic enzymes and demonstrates that the low amount of $CO_2$ detected on Day 1 is due to pancreatic insufficiency.

EXAMPLE 2

The materials and methods used to detect pancreatic exocrine insufficiency were the same as described in Example 1 with the following exceptions. In place of $^{14}C$-labelled cholesterol octanoate mixture A contains 200 mg of cholesterol-1-13 octanoate containing 4 micromoles $^{13}C/Kg$ and 5 microcuries of octanoate-1-$^{14}C$. The former compound was donated by Stohler Isotopec Chemicals, Walham, MA, while the latter was purchased from New England Nuclear Corp., Boston, MA.

Figure 2:
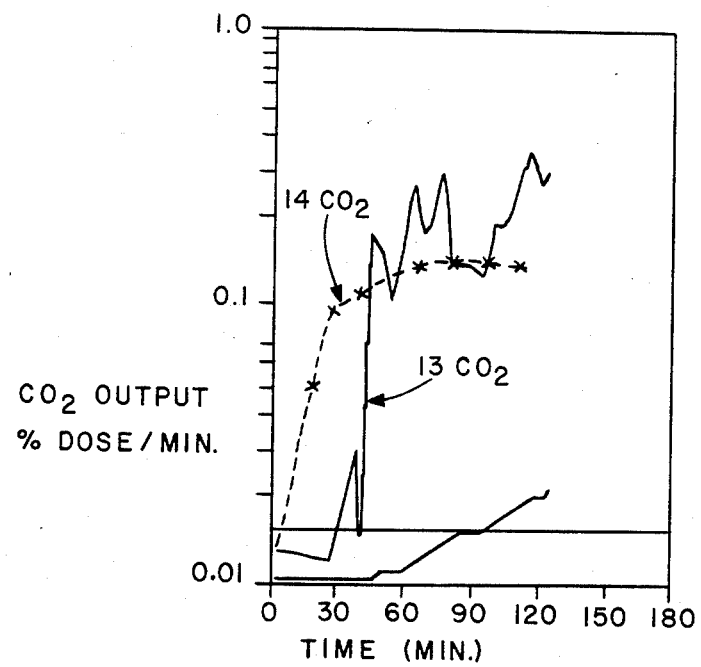
FIG. 2 shows breath $CO_2$ measured after ingesting a meal containing cholesterol-1-$^{13}C$-octanoate and octanoate-1-$^{14}C$. The % dose/minute of $CO_2$ expired as $^{13}CO_2$ and $^{14}CO_2$ is shown.

The amounts of $CO_2$ expired as $^{13}CO_2$ and $^{14}CO_2$ was determined by on-line analysis using an infrared analyzer and liquid scintillation counting respectively. FIG. 2 shows the results obtained.

EXAMPLE 3

The materials and methods used to detect pancreatic exocrine insufficiency in animals are the same as those used in Example 1 with the following exceptions. To perform the test rats were made pancreatic insufficient by injecting the pancreatic duct by zein as described by Rhodes and coworkers in *Clinical Research*, Vol. 29, p. 713 (1981), which includes injecting about 0.1 ml of a solution containing 37 mg of zein dissolved in 0.075 ml of 95% ethanol and mixed in 1 ml of linoleic and oleic acids, the latter being present in a weight ratio of 2:1.

An emulsion of 4.4 microcuries of $^{14}C$-labelled cholesterol octanoate was prepared by sonication for 20 minutes, of a mixture containing 50 mg of cholesterol-free vegetable oil, 60 mg of egg yolk lecithin and 5 mg of non-radioactive cholesterol octanoate in 2.5 ml of saline, 0.5 ml of this mixture with or without exogenously added pancreatic enzymes was fed intragastrically to rats and their breath $^{14}CO_2$ collected quantitatively by trapping in ethanolamine-methyl cellosolve, 1:1, V:V. The results of a typical test are shown in FIG. 3 which shows that there is a dramatic reduction in the amount of radioactive $CO_2$ in the breath with time of rats that do not receive exogenous pancreatic enzymes (Curve B), compared to those that did (Curve A).

We claim:

1. A method for determining pancreatic exocrine function in a patient's body comprising the patient ingesting an ester R2COOR1 where R1 is a sterol group, and R2 is a traceable hydrocarbon group oxidizable to traceable carbon dioxide in the body, said traceable carbon dioxide being expired from the body in the breath, and detecting the rate of appearance of said traceable carbon dioxide in the breath of said patient and comparing the rate of appearance of said traceable carbon dioxide produced when said ester is ingested alone with the rate of traceable carbon dioxide produced when said ester is ingested with exogenously added pancreatic enzymes suitable for hydrolyzing said ester as an indication of pancreatic exocrine function.

2. A method according to claim 1 wherein said R2 traceable hydrocarbon group comprises from 2 to 10 carbon atoms.

3. A method according to claim 2 wherein said traceable R2 hydrocarbon group comprises one or more carbon atoms of either $^{14}C$ or $^{13}C$.

4. A method according to claim 3 wherein the ester is prepared for patient injestion by combining said ester with a triglyceride in solution and agitating said solution forming a lipid matrix of triglyceride situated about said ester and suspending said lipid matrix in an aqueous solution.

5. A method for determing pancreatic exocrine function in a patient's body comprising the patient ingesting simultaneously an ester R2COOR1, and a salt of a fatty acid R3COOH, wherein R1 is a sterol group, and R2 and R3 are differentially traceable groups oxidizable to differentially traceable carbon dioxides in the body, said differentially traceable carbon dioxides being expired from said body in the breath and detecting said differentially traceable carbon dioxides in the breath of said patient, and comparing the rates of appearance of said differentially traceable carbon dioxides as an indication of pancreatic exocrine function.

6. A method according to claim 5 wherein said R2 group comprises from 2 to 10 carbon atoms and one or more of said carbon atoms is $^{14}C$ or $^{13}C$.

7. A method according to claim 6 wherein R3 comprises from 2 to 10 carbon atoms and one or more of said carbon atoms is labelled with $^{14}C$ or $^{13}C$.

8. A method according to claim 7 wherein R1 is cholesterol.

9. A method according to claim 8 wherein said ester is cholesterol octanoate.

10. A method according to claim 9 wherein said salt of said fatty acid is an octanoate salt.

11. A method according to claim 8 wherein said ester, and said salt of said fatty acid are prepared for patient ingestion by combining said ester and said fatty acid salt with a triglyceride in solution, and agitating said solution thereby forming a lipid matrix of said triglyceride situated about said ester and fatty acid salt and suspending said lipid matrix in an aqueous solution.

12. A composition useful for determining pancreatic exocrine function prepared by combining in aqueous solution a triglyceride, cholesterol octanoate, and an octanoate salt, and agitating said solution to form a lipid matrix, said lipid matrix comprising said triglyceride, cholesterol octanoate, and octanoate salt, and said cholesterol octanoate and octanoate salt exhibiting one or more different traceable isotopes of carbon detectable as carbon dioxide.

* * * * *

UNITED STATES PATENT AND TRADEMARK OFFICE
CERTIFICATE OF CORRECTION

PATENT NO. : 4,676,974

DATED : June 30, 1987

INVENTOR(S) : Alan F. Hofmann, et al

It is certified that error appears in the above-identified patent and that said Letters Patent is hereby corrected as shown below:

Claim 7, column 6, line 46, after "with"

insert --either--

Signed and Sealed this

Twenty-fourth Day of November, 1987

Attest:

DONALD J. QUIGG

*Attesting Officer*  *Commissioner of Patents and Trademarks*